United States Patent [19]

Shiono

[11] Patent Number: 4,457,184

[45] Date of Patent: Jul. 3, 1984

[54] FLUID PIPETTING METHOD

[75] Inventor: Kazuo Shiono, Oume, Japan

[73] Assignee: Olympus Optical Company, Ltd., Japan

[21] Appl. No.: 459,648

[22] Filed: Jan. 20, 1983

[30] Foreign Application Priority Data

Jan. 29, 1982 [JP] Japan .................................. 57-11774

[51] Int. Cl.³ .............................................. B01L 3/02
[52] U.S. Cl. .................................. 73/864.11; 422/100
[58] Field of Search ........... 73/863.32, 864.01, 864.02, 73/864.11, 864.12, 864.13, 864.15, 864.16, 864.17, 864.18, 864.21, 864.22, 864.23, 864.24, 864.25; 422/100

[56] References Cited

U.S. PATENT DOCUMENTS 3,188,181 6/1965 Peterson et al. .................... 422/100
3,666,420 5/1972 Phatzsch ......................... 73/864.12

Primary Examiner—S. Clement Swisher
Attorney, Agent, or Firm—Ostrolenk, Faber, Gerb & Soffen

[57] ABSTRACT

A fluid pipetting method is to pipette and distribute a fluid into a plurality of vessels by means of a single probe. In pipetting operations, a cleaning liquid, an air layer and the total sum of the fluid including a part of surplus, the total of the fluid to be pipetted and a part of waste are picked up into the probe in the order listed and an amount of pipetting the fluid into respective vessels is controlled in accordance with the pipetting order in such a manner that the amount of the fluid pipetted and distributed into each of vessels is substantially a given value.

5 Claims, 5 Drawing Figures

FLUID PIPETTING METHOD

BACKGROUND OF THE INVENTION

The present invention relates to a test fluid pipetting method, and more particularly, to such a method for pipetting and distributing each of a plurality of test fluids into a plurality of containers by means of a common pipetting apparatus.

By way of example, there have been proposed the multichannel type automatic analyzers which chemically and simultaneously analyze a plurality of components contained in a blood serum and other apparatus which automatically and simultaneously conduct multiple immunological inspections on the same test fluid based on agglutination by antigens and antibodies. In such apparatus, a plurality of test fluids are generally transferred successively (by picking them up) into respective containers and these test fluids in respective containers are pipetted and distributed successively into each of a plurality of reaction vessels corresponding to the number of analyzing items by means of a common pipetting apparatus. In the procedure in which successive test fluids are pipetted and distributed by means of the common pipetting apparatus, contamination and variation of concentration between test fluids being successively pipetted have an adverse effect upon results of the analysis. Therefore, it is necessary to effectively prevent such disadvantage.

By way of example, in an arrangement of an automatic chemical test apparatus disclosed in the Japanese Patent Publication No. Sho 50 - 17878, as shown in FIG. 1, a probe 1 for picking up and discharging a test fluid is connected through a tube 2 and couplings 3 and 4 to a pipetting syringe 5 and a syringe 6 for cleaning water and is connected through coupling 3 to a syringe 7 for forming an air layer. The pipetting operations of the arrangement are as follows. First, under the condition in which the probe 1 is immersed in water, the probe 1 and the tube 2 are cleaned by operating the syringe 6 and then water 8 is sucked into the probe 1 and the tube 2. Second, under the condition in which the probe 1 is placed in the air, air is drawn into the probe 1 by means of the syringe 7 and then upon once immersing the probe 1 into a test fluid held within a vessel a predetermined amount of the test fluid is sucked into the probe 1 by means of the syringe 5. Thereafter, the probe 1 is placed in the air and air is again drawn into the probe 1 by means of syringe 7. Subsequently, the probe 1 is immersed again into the same test fluid as previously sucked in and a predetermined amount of the test fluid is picked up by means of the syringe 5. Thus, as shown in FIG. 1, each layer of water 8, air 9, test fluid 10, air 11 and test fluid 12 is formed successively in the probe 1 and the tube 2. In this case, the test fluids 10 and 12 are the same but the test fluid 10 is for cleaning, not pipetted into a reaction tube. In addition, the test fluid 12 is drawn in in excess of the total amount to be pipetted into a plurality of reaction tubes.

After one of test fluids is drawn in as stated above, a part of the test fluid 12 is discharged into the test fluid vessel and then the test fluid 12 is successively pipetted by a predetermined amount thereof into a required number of reaction tubes. Subsequently, a surplus of the test fluid 12 and the test fluid 10 are discharged into a waste fluid vessel. Thus the pipetting and distributing operations of one of test fluids concerned are completed. Thereafter, the above sequential operations are repeated with regard to each of other test fluids to distribute the same into a plurality of the reaction tubes.

According to such pipetting and distributing method, the inner and outer walls of the probe 1 and the inner wall of the tube 2 are initially cleaned with water in the pipetting operations of each of test fluids so that it is possible to prevent occurrence of contamination between the successive test fluids being pipetted. Also, since the test fluid layer 12 to be pipetted into a plurality of reaction tubes is separated through air layer 11, test fluid layer 10 and air layer 9 from water layer 8, the dilution of the test fluid 12 by water 8 can be reduced and therefore it is possible to distribute the same test fluid having substantially a given concentration into each of reaction tubes. However, with the pipetting method, in which the same test fluid is picked up by separating it through air layers 9 and 11, it is necessary to pull out the probe 1 from the test fluid once while picking up it. Thus, the pipetting and distributing operations of each test fluid are time-consuming and hence it is impossible to conduct them rapidly.

Additionally, the Japanese Patent Laying-Open No. Sho 55 - 71950 discloses another pipetting and distributing method in which a test fluid in excess of the total amount needed for distribution is drawn into a fluid pipetting conduit into which a throwing-away liquid such as a diluent has been drawn, through an air layer and after the test fluid thus sucked in is partially discharged together with the throwing-away liquid which is ejected from another liquid conduit, the test fluid is pipetted in the similar manner as previously described into a plurality of reaction tubes together with a throwing-away liquid and subsequently the remaining test fluid and throwing-away liquid are successively discharged from the pipetting conduit to clean the inner wall of the latter. In such pipetting and distributing method in which a test fluid to be pipetted is drawn into the pipetting conduit by separating the test fluid from a throwing-away liquid through an air layer, there is no necessity for pulling out the pipetting conduit from the test fluid while drawing in the latter as in the pipetting and distributing method disclosed in the Japanese Patent Publication No. Sho 50 - 17878 described previously. Accordingly, it is possible to conduct the pipetting and distributing operations of a test fluid in a short time. However, when a test fluid to be pipetted and a throwing-away liquid for cleaning are separated through only an air layer, the test fluid within the pipetting conduit is subject to the influence of dilution by the throwing-away liquid adhered to the inner wall of the conduit during the previous cleaning in proportion as the test fluid within the conduit is substantially nearer to the throwing-away liquid. Consequently, when the test fluid drawn into the tube is pipetted and distributed to a plurality of reaction tubes by a given amount thereof, its concentration is reduced in proportion as the pipetting order is later, that is, the test fluid becomes closer to the throwing-away liquid, and general disadvantages are that it is hard to conduct an analysis with high accuracy.

SUMMARY OF THE INVENTION

It is an object of the invention to provide a test fluid pipetting and distributing method to solve various problems noted above and to pipette and distribute each of a plurality of test fluids rapidly and successively with substantially a predetermined concentration.

According to the invention, it is possible to maintain substantially the equal pipetting amount of a test fluid irrespective of pipetting order by supplementing the pipetting amount of the test fluid at every pipetting order in accordance with the degree that concentration of the test fluid is reduced by dilution thereof with cleaning liquid. Besides, it is possible to shorten the pipetting cycle since it is not necessity to engage in complicated operations for forming a plurality of air layers within a probe in order to prevent reduction of the concentration.

DESCRIPTION OF PREFERRED EMBODIMENTS

Figure 1:
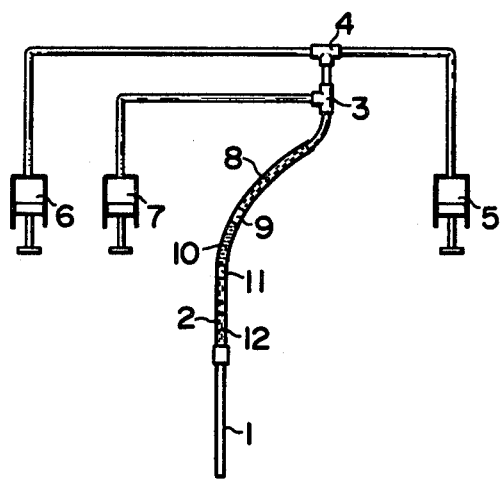
FIG. 1 is a schematic diagram of a pipetting apparatus to explain an example of conventional pipetting methods.
Figure 2:
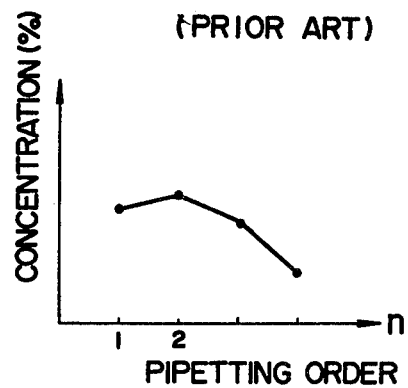
FIG. 2 is a graph showing concentration of a test fluid distributed by another conventional pipetting method.
Figure 3:
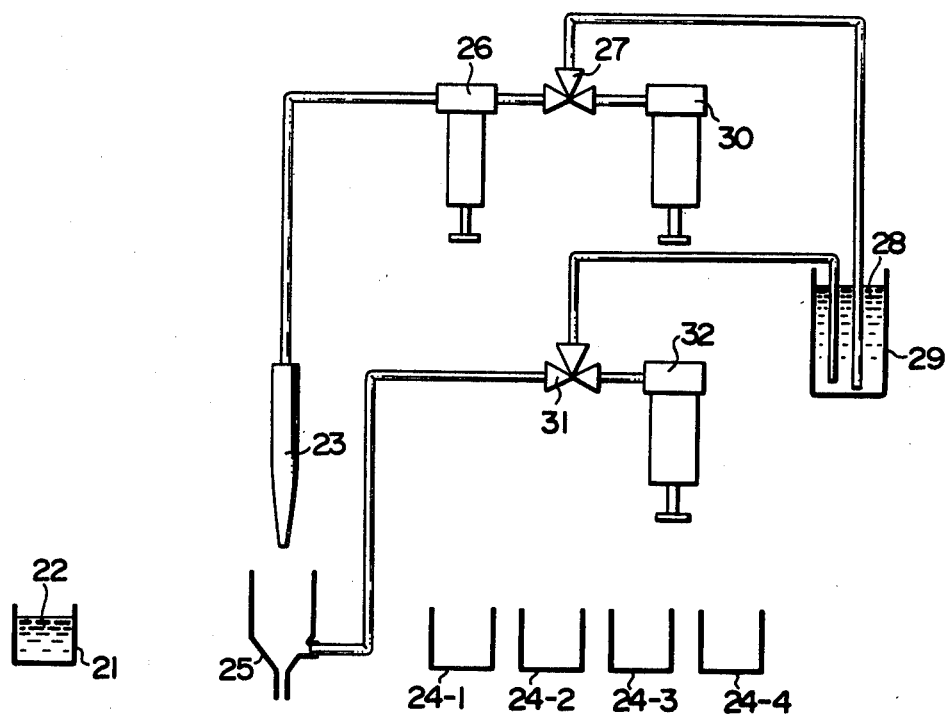
FIG. 3 is a schematic diagram illustrating a structure of an embodiment of a pipetting apparatus implementing a pipetting method of the present invention.

Referring now to FIG. 3, each of a plurality of test fluids 22 which are contained within respective test fluid cups 21 and are to be conveyed sequentially is selectively pipetted into four reaction tubes 24-1 through 24-4 utilizing a common probe 23. To this end, the probe 23 is provided in such a manner that it is movable between a predetermined fluid picking up station at which test fluid cup 21 is disposed, a cleaning station at which a cleaning tank 25 is disposed and each of fluid pipetting stations corresponding to respective dispositions of four reaction tubes 24-1 through 24-4 and also it is able to enter the cup 21 and the cleaning tank 25 at both the fluid picking up and the cleaning stations. The probe 23 is connected through a syringe 26 for pipetting the test fluid and an electromagnetic valve 27 to a cleaning liquid tank 29 which contains a cleaning liquid 28 as well as to a syringe 30 for picking up and discharging the cleaning liquid. Further, the cleaning tank 25 is connected through an electromagnetic valve 31 to the cleaning liquid tank 29 and a syringe 32 for picking up and discharging the cleaning liquid.

Figure 4:
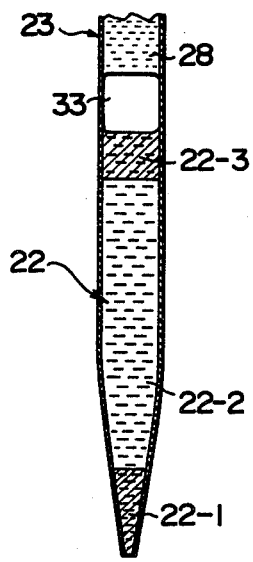
FIG. 4 is a magnified view in cross section of the essential part of a probe to explain contents of the test fluid drawn into the probe shown in FIG. 3.
Figure 5:
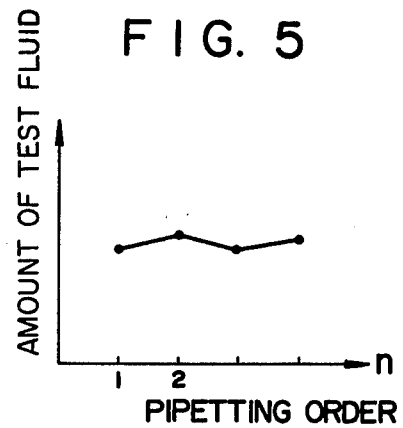
FIG. 5 is a graph showing concentration of the test fluid distributed by the method of the invention.

In operation, first, cleaning liquid 28 is discharged through the probe 23 by operating the syringe 30 at the cleaning station and cleaning liquid 28 is ejected into the cleaning tank 25 by operating the syringe 32 to clean the inner and outer walls of the probe 23 and thereafter cleaning liquid 28 is picked up into the probe 23 and a flow line communicating therewith. Next, after air is drawn into the probe 23 by operating the syringe 26 slightly while the probe 23 is transferred to the picking up station, the probe 23 is immersed into test fluid 22 at the picking up station and under such condition the test fluid 22 is again drawn into the probe 23 separating it through an air layer 33 from cleaning liquid 28 as shown in FIG. 5 by operating the syringe 26. The contents of the test fluid 22 thus picked up, as shown in FIG. 4, in the embodiment of the invention, are composed of waste test fluid 22-1, substantial test fluid to be pipetted 22-2 and surplus test fluid 22-3. The waste test fluid 22-1 is discharged prior to pipetting into the reaction tubes 24-1 through 24-4. This discharging operation is to prevent a variation in amount of the test fluid pipetted into each of the reaction tubes due to a variation of the degree in which the test fluid adheres to the tip of probe 23 between the times when the probe 23 is pulled out from the test fluid cup 21 and when the test fluid is ejected. The amount of substantial test fluid 22-2 is equal to the total of the test fluids to be selectively pipetted into four reaction tubes 24-1 through 24-4. Considering that the concentration of the test fluid is reduced by a dilution effect of cleaning fluid 28 as the test fluid becomes closer to the cleaning liquid as previously mentioned, an amount of the test fluid to be picked up for a later pipetting order is rather much in the embodiment. The surplus test fluid 22-3 is to prevent reduction in pipetting accuracy resulting from the fact that if the test fluid 22-2 were separated from cleaning liquid 28 only through air layer 33, the substantial test fluid when being pipetted finally would be scattered by discharge of air layer 33 or left hanging down like a raindrop at the tip of probe 23.

After the test fluid 22 is picked up into the probe 23 through air layer 33 as described above, the probe 23 is transferred to the first pipetting station through the cleaning station. During the time that the probe 23 is raised while it is leaving the surface of test fluid 22 within the cup 21 to the time it is leaving the station of test fluid cup 21 or the probe 23 passes through the cleaning station, the waste test fluid 22-1 is discharged through the probe 23 by slightly operating the syringe 26. Then, the probe 23 is transferred successively to each of pipetting stations corresponding to reaction tubes 24-1 through 24-4 and the substantial amount of test fluid 22-2 is pipetted and distributed thereinto respectively by operating the syringe 26. At this time, it is to be noted that the amount of fluid which is pipetted into each successive reaction tube is increased (due to dilution of the test fluid) so that the amount of test fluid distributed in every pipetting order may be substantially a given value. The total amount of fluid to be pipetted in successive pipetting orders is experimentally determined depending upon a probe to be used since the dilution effect upon the test fluid 22 drawn in the probe 23 varies with the inner diameter, material, etc. thereof.

Upon completion of the required operations for pipetting and distributing into reaction tubes 24-1 through 24-4, the probe 23 is transferred to the cleaning station and then the surplus test fluid 22-3 is discharged into the cleaning tank 25 by operating the syringe 26 to complete the pipetting and distributing operation for the test fluid concerned. Thereafter, each of other test fluids contained within respective test fluid cups 21 which are conveyed sequentially to the fluid picking position is pipetted and distributed successively by repeating the sequential operations described above.

As indicated in the foregoing, it is possible in the present embodiment to make the total amount of test fluid in each pipetting operation substantially constant as shown in FIG. 5 since the total pipetting amount fluid is supplemented in proportion to the degree that concentration of the distributed test fluid is reduced by penetration of cleaning water 28 so that the test fluid pipetted in each pipetting order may be substantially a given amount. In addition, there is no necessity of forming a plurality of air layers within a probe as shown in the previously cited Japanese Patent Publication No.

Sho 50 - 17878 to prevent reduction of concentration so that rapid pipetting and distribution of each of successive test fluids can be effected by the method of the invention.

It is to be understood that the invention is not limited only to the specific embodiment described above and many modifications and variations of the invention are possible. By way of example, while, in the embodiment described above, the test fluid 22 is picked up into the probe 23 through the air layer 33 under the condition in which the cleaning liquid 28 has been filled within the probe 23, it is possible to effectively apply the invention to the case that the probe 23 is cleaned by sucking and discharging the cleaning liquid and then the test fluid is pipetted by picking up only the test fluid without picking up the cleaning liquid into the probe. Additionally, while the test fluid is pipetted rather much by picking up it substantially in excess of the amount according to later successive pipetting orders in the above embodiment, it is to be understood that the same effect can be obtained by pipetting the test fluid of a smaller amount according to the earlier pipetting orders so that the distributed test fluid has substantially a given amount.

What is claimed is:

1. A method for pipetting and distributing each of a plurality of test fluids into a plurality of vessels by means of a common pipetting apparatus, the method comprising the steps of:
   (A) cleaning the inner and outer walls of a probe provided in the pipetting apparatus by means of a cleaning liquid at a cleaning station of said apparatus;
   (B) placing cleaning liquid within said probe and a fluid line communicating therewith;
   (C) drawing air into said probe while transferring said probe to a station for picking up said fluid so as to define an air layer in said probe;
   (D) drawing test fluid into said probe while said probe is immersed in a reservoir of test fluid in such a manner that said test fluid drawn into said probe is separated from said cleaning liquid in said probe through said air layer;
   (E) discharging a part of said test fluid from said probe after said probe has been withdrawn from the surface of said reservoir of test fluid but before said probe reaches a first fluid pipetting station at which one of said vessels is located;
   (F) successively transferring said probe to each of a plurality of fluid pipetting stations corresponding to each of said vessels, respectively, and pipetting a varying amount of fluid from said probe into each said vessel, said fluid being defined by test fluid and an amount of cleaning liquid which migrates into said test fluid while in said probe, the amount of fluid pipetted varying in accordance with the order in which said probe is transferred to said pipetting stations such that the amount of the test fluid pipetted into respective vessels is maintained at a substantially constant value;
   (G) returning said probe to said cleaning station after said fluid has been pipetted into all of said vessels and then discharging any test fluid which remains in said probe; and thereafter
   (H) repeating steps (A) through (G) for each of said plurality of test fluids.

2. A method according to claim 1, in which the amount of the fluid pipetted into each successive vessel in step (F) is increased for each successive vessel.

3. A method according to claim 1, in which the amount of the fluid pipetted in step (H) is lower for earlier pipetted vessels than later pipetted vessels.

4. A method according to either claim 2 or claim 3, in which the degree to which the amount fluid pipetted varies for successive pipetting operations is determined by the inner diameter and material of a probe to be used.

5. A method according to claim 1, in which the fluid is pipetted and distributed by picking up by itself without picking up a cleaning liquid into the probe after the latter is cleaned by the cleaning liquid.

* * * * *